(12) United States Patent
Kwon et al.

(10) Patent No.: US 8,369,958 B2
(45) Date of Patent: Feb. 5, 2013

(54) INDEPENDENT AND CONCURRENT PROCESSING MULTIPLE AUDIO INPUT SIGNALS IN A PROSTHETIC HEARING IMPLANT

(75) Inventors: Bomjun Kwon, Aurora, CO (US); Christopher van den Honert, Aurora, CO (US)

(73) Assignee: Cochlear Limited, Macquarie University, NSW (AU)

( * ) Notice: Subject to any disclaimer, the term of this patent is extended or adjusted under 35 U.S.C. 154(b) by 563 days.

(21) Appl. No.: 11/335,563

(22) Filed: Jan. 20, 2006

(65) Prior Publication Data
US 2006/0265061 A1 Nov. 23, 2006

Related U.S. Application Data

(60) Provisional application No. 60/682,388, filed on May 19, 2005.

(51) Int. Cl.
*A61N 1/00* (2006.01)
*A61N 5/04* (2006.01)

(52) U.S. Cl. ............... 607/57; 607/50; 607/55; 600/372

(58) Field of Classification Search .................... 607/50, 607/55, 57; 600/372
See application file for complete search history.

(56) References Cited

U.S. PATENT DOCUMENTS

| | | | |
|---|---|---|---|
| 4,284,856 A * | 8/1981 | Hochmair et al. ................. | 607/9 |
| 4,515,158 A | 5/1985 | Patrick et al. | |
| 4,593,696 A | 6/1986 | Hochmair et al. | |
| 4,813,417 A | 3/1989 | Soli et al. | |
| 4,823,795 A | 4/1989 | van den Honert | |
| 5,095,904 A | 3/1992 | Seligman et al. | |
| 5,531,774 A | 7/1996 | Schulman et al. | |
| 5,597,380 A * | 1/1997 | McDermott et al. ............ | 607/57 |
| 5,776,172 A * | 7/1998 | Schulman et al. .............. | 607/56 |

(Continued)

FOREIGN PATENT DOCUMENTS

| | | |
|---|---|---|
| AU | 2001265692 | 1/2002 |
| EP | 0661905 | 7/1995 |

(Continued)

OTHER PUBLICATIONS

Non-Final Office Action issued in U.S. Appl. No. 11/030,980, mailed Aug. 27, 2009, 11 pages.

(Continued)

*Primary Examiner* — Nicole F Lavert
(74) *Attorney, Agent, or Firm* — Kilpatrick, Townsend & Stockton, LLP (57) ABSTRACT

A prosthetic hearing implant capable of independently and concurrently processing multiple audio input signals such that each audio input signal is separately utilized to stimulate the basilar membrane of the implant recipient. A prosthetic hearing implant of the present invention simultaneously receives discrete audio signals from each of one or more audio sources, generates a separate set of one or more stimulations signals for each audio signal, and concurrently applies the stimulation signals to the cochlear. Different channels of stimulation may be allocated to each audio input signal. Alternatively, different modes of stimulation may be used for each input signal. Or, in yet another example, the audio input signals may be time-multiplexed such that the input signals are applied in alternating timeslots. Or, in yet other examples, the input signals may be applied using a combination of stimulation channels, modes of stimulation, and alternating time slots. The stimulation signals may be delivered to the same or different electrodes depending on the quantity and frequency component of the received audio input signals, the quantity of available stimulation channels, and other factors.

39 Claims, 4 Drawing Sheets

U.S. PATENT DOCUMENTS

| | | | |
|---|---|---|---|
| 5,876,443 A * | 3/1999 | Hochmair et al. | 623/10 |
| 5,999,859 A * | 12/1999 | Jolly | 607/137 |
| 6,219,580 B1 * | 4/2001 | Faltys et al. | 607/57 |
| 6,272,382 B1 * | 8/2001 | Faltys et al. | 607/57 |
| 6,289,247 B1 * | 9/2001 | Faltys et al. | 607/57 |
| 6,321,125 B1 * | 11/2001 | Kuzma | 607/137 |
| 6,390,971 B1 * | 5/2002 | Adams et al. | 600/25 |
| 6,480,820 B1 | 11/2002 | Clopton et al. | |
| 6,572,531 B2 * | 6/2003 | Zilberman et al. | 600/25 |
| 6,604,283 B1 * | 8/2003 | Kuzma | 29/857 |
| 6,611,717 B1 | 8/2003 | Clark et al. | |
| 6,732,073 B1 * | 5/2004 | Kluender et al. | 704/233 |
| 6,778,858 B1 | 8/2004 | Peeters | |
| 6,915,166 B1 * | 7/2005 | Stecker et al. | 607/55 |
| 6,920,360 B2 * | 7/2005 | Lee et al. | 607/60 |
| 7,082,332 B2 | 7/2006 | Blamey et al. | |
| 7,103,417 B1 | 9/2006 | Segel et al. | |
| 7,251,530 B1 * | 7/2007 | Overstreet et al. | 607/55 |
| 7,292,892 B2 * | 11/2007 | Litvak et al. | 607/57 |
| 7,729,775 B1 | 6/2010 | Saoji et al. | |
| 2003/0059076 A1 | 3/2003 | Martin | |
| 2003/0135247 A1 * | 7/2003 | Zierhofer | 607/60 |
| 2003/0171786 A1 | 9/2003 | Blamey et al. | |
| 2004/0015210 A1 | 1/2004 | Clark et al. | |
| 2004/0052391 A1 | 3/2004 | Bren et al. | |
| 2004/0066944 A1 * | 4/2004 | Leenen et al. | 381/314 |
| 2004/0136556 A1 | 7/2004 | Litvak et al. | |
| 2005/0010267 A1 * | 1/2005 | Ibrahim | 607/57 |
| 2005/0177205 A1 | 8/2005 | Kwon et al. | |
| 2005/0187592 A1 | 8/2005 | Seligman et al. | |
| 2005/0192646 A1 | 9/2005 | Grayden et al. | |
| 2005/0248158 A1 | 11/2005 | Westerkull | |
| 2006/0080087 A1 | 4/2006 | Vandali et al. | |
| 2006/0212095 A1 | 9/2006 | Wolfe et al. | |
| 2007/0173962 A1 | 7/2007 | Rasmussen | |
| 2008/0234783 A1 | 9/2008 | van den Honert | |

FOREIGN PATENT DOCUMENTS

| | | |
|---|---|---|
| JP | 2007-172955 | 5/2007 |
| WO | 01/99470 | 12/2001 |
| WO | WO-2004021363 | 3/2004 |
| WO | WO-2005057983 | 6/2005 |

OTHER PUBLICATIONS

Final Office Action issued in U.S. Appl. No. 11/030,980, mailed Apr. 14, 2010, 15 pages.
Non Final Office Action issued in U.S. Appl. No. 11/030,980, mailed Jul. 19, 2010, 19 pages.
Non-Final Office Action issued in U.S. Appl. No. 11/030,980, mailed Mar. 25, 2008, 8 pages.
Final Office Action issued in U.S. Appl. No. 11/030,980, mailed Dec. 19, 2008, 9 pages.
Final Office Action issued in U.S. Appl. No. 11/723,696, mailed Jan. 27, 2010, 14 pages.
Non-Final Office Action issued in U.S. Appl. No. 11/723,696, mailed Jul. 8, 2009, 15 pages.
Final Office Action issued in U.S. Appl. No. 11/030,980, mailed Jan. 20, 2011 16 pages.
Non-Final Office Action issued in U.S. Appl. No. 11/723,696, mailed Nov. 26, 2010 30 pages.
Australian Office Action dated Apr. 3, 2009 for AU 2005200067.
International Search Report for PCT/US08/057690 dated Aug. 29, 2008.
Written Opinion for PCT/US08/057690 dated Aug. 29, 2008.
Robles et al., "Mechanics of the Mamalian Cochlear," Physiological Reviews, vol. 81, No. 3, pp. 1305-1352, Jul. 3, 2001.
European Search Report for European Patent Application 08744124.2 dated May 20, 2010.
International Preliminary Report on Patentability for International Application No. PCT/US08/57690 dated Feb. 27, 2009.

* cited by examiner

INDEPENDENT AND CONCURRENT PROCESSING MULTIPLE AUDIO INPUT SIGNALS IN A PROSTHETIC HEARING IMPLANT

RELATED APPLICATIONS

This application claims priority from U.S. Provisional Application No. 60/682,388 filed May 19, 2005, entitled "Alternating Use of Channels in Speech Processing with Multiple Inputs," which is hereby incorporated by reference herein in its entirety.

BACKGROUND

1. Field of the Invention

The present invention relates generally to a prosthetic hearing implant and, more particularly, to independently and concurrently processes multiple audio input signals in a prosthetic hearing implant.

2. Related Art

There are a variety of medical implants which deliver electrical stimulation to a patient or recipient ("recipient" herein) for a variety of therapeutic benefits. For example, the hair cells of the cochlea of a normal healthy ear convert acoustic signals into nerve impulses. People who are profoundly deaf due to the absence or destruction of cochlea hair cells are unable to derive suitable benefit from conventional hearing aid systems. Prosthetic hearing implants have been developed to provide such persons with the ability to perceive sound. Prosthetic hearing implants bypass the hair cells in the cochlea to directly deliver electrical stimulation to auditory nerve fibers, thereby allowing the brain to perceive a hearing sensation that resembles the natural hearing sensation.

The electrodes implemented in stimulating medical implants vary according to the device and tissue which is to be stimulated. For example, the cochlea is tonotopically mapped and partitioned into regions, with each region being responsive to stimulus signals in a particular frequency range. To accommodate this property of the cochlea, prosthetic hearing implant systems typically include an array of electrodes each constructed and arranged to deliver appropriate stimulating signals to particular regions of the cochlea, each representing a different frequency component of a received audio signal.

Currently, most prosthetic hearing implant recipients have difficulty understanding speech in a noisy environment. With the moderate signal-to-noise ratios which are somewhat tolerable by normal hearing listeners, such as zero to five decibels (dB), speech reception by hearing implant recipients is dramatically reduced. Considering that only limited speech information is available through the hearing implant, this reduction in capability is, to a certain degree, unavoidable.

Noise and speech sources are often spatially separated. The ability of normal hearing individuals to differentiate between multiple distinct sources of sound is often due in part to the listener's ability to use spatial hearing to distinguish between multiple sound sources. In contrast, conventional prosthetic hearing implants intermingle or combine multiple sound signals into a single audio signal which is presented to the cochlear. As a result, hearing implant recipients are unable to differentiate between two or more different streams of auditory input. For example, in contrast to a hearing implant recipient, normal hearing listeners are typically able to participate in a conversation with a person in their immediate vicinity while simultaneously hearing background music.

SUMMARY

In accordance with one aspect of the present invention, a prosthetic hearing implant is disclosed. The hearing implant is constructed and arranged to independently and concurrently process a plurality of audio input signals received via separate audio sources and to separately utilize each of said plurality of audio input signals to stimulate a basilar membrane of a recipient of the hearing implant.

In accordance with another aspect of the present invention, a method for stimulating a cochlea of a recipient of a prosthetic hearing implant is disclosed. The method comprises: simultaneously receiving discrete audio signals from each of one or more audio sources; generating a separate set of one or more stimulations signals for each of said audio signals; and concurrently applying said set of one or more stimulation signals to the cochlea.

In a still further aspect of the invention, a method of neural stimulation is disclosed. The method comprises: receiving a first audio signal each from a first of a plurality of audio sources; receiving a second audio signal from a second of a plurality of audio sources; generating a first set of one or more stimulation signals corresponding to said first audio signal; generating a second set of one or more stimulation signals corresponding to said second audio signal; and applying stimuli to a recipient's cochlea using the first and second sets of stimulation signals.

In another aspect of the invention, a system for neural stimulation is disclosed. The system comprises: at least one audio pickup device capable of receiving at least a first acoustical signal and a second acoustical signal; a speech processing unit capable of generating a first set of one or more stimulation signals for application of the first audio signal, and generating a second set of one or more stimulation signals for application of the second audio signal; and an implant capable of applying stimuli to a recipient using the generated first and second sets of stimulation signals.

BRIEF DESCRIPTION OF THE DRAWINGS

Embodiments of the present invention are described herein in conjunction with the accompanying drawings, in which.

DETAILED DESCRIPTION

Aspects of the present invention are generally directed to a prosthetic hearing implant capable of independently and concurrently processing multiple audio input signals such that each audio input signal is separately utilized to stimulate the basilar membrane of the implant recipient. A prosthetic hearing implant of the present invention simultaneously receives discrete audio signals from each of one or more audio sources, generates a separate set of one or more stimulations signals for each audio signal, and concurrently applies the stimulation signals to the cochlea. Different channels of stimulation may be allocated to each audio input signal. Alternatively, different modes of stimulation may be used for each input signal. Or, in yet another example, the audio input signals may be time-multiplexed such that the input signals are applied in alternating timeslots. Or, in yet other examples, the input signals may be applied using a combination of stimulation channels, modes of stimulation, and alternating time slots. The stimulation signals may be delivered to the same or different electrodes depending on the quantity and frequency component of the received audio input signals, the quantity of available stimulation channels, and other factors. Advantageously, recipients of a hearing prosthesis implementing an embodiment of the present invention may be capable of segregating the perceived audio signals; that is, the recipient is provided the opportunity to make use of spatial hearing. Such a capability may enable the recipient to distinguish between multiple sources of sound simultaneously received by the recipient.

Embodiments of the present invention are described herein primarily in connection with one type of stimulating medical device, a prosthetic hearing implant system. Prosthetic hearing implant systems include but are not limited to hearing aids, auditory brain stimulators, and COCHLEAR™ prostheses (commonly referred to as COCHLEAR™ prosthetic devices, COCHLEAR™ implants, COCHLEAR™ devices, and the like; collectively COCHLEAR™ implants herein.) COCHLEAR™ is a trademark of Cochlear Limited, Lane Cove Australia. For ease of reading, COCHLEAR™ implants will be referred to simply herein as "cochlear implants." The use of "cochlear" without capitalization or accompanying notation should not be construed as having any negative impact on Cochlear Limited's trademark, but rather is used merely to facilitate a reader's understanding of embodiments of the present invention. Cochlear implants use direct electrical stimulation of auditory nerve cells to bypass absent or defective hair cells that normally transduce acoustic vibrations into neural activity. Such devices generally use an electrode array inserted into the scala tympani of the cochlea so that the electrodes may differentially activate auditory neurons that normally encode differential pitches of sound. Auditory brain stimulators are used to treat a smaller number of recipients with bilateral degeneration of the auditory nerve. For such recipients, the auditory brain stimulator provides stimulation of the cochlear nucleus in the brainstem, typically with a planar electrode array; that is, an electrode array in which the electrode contacts are disposed on a two dimensional surface that can be positioned proximal to the brainstem.

Figure 1:
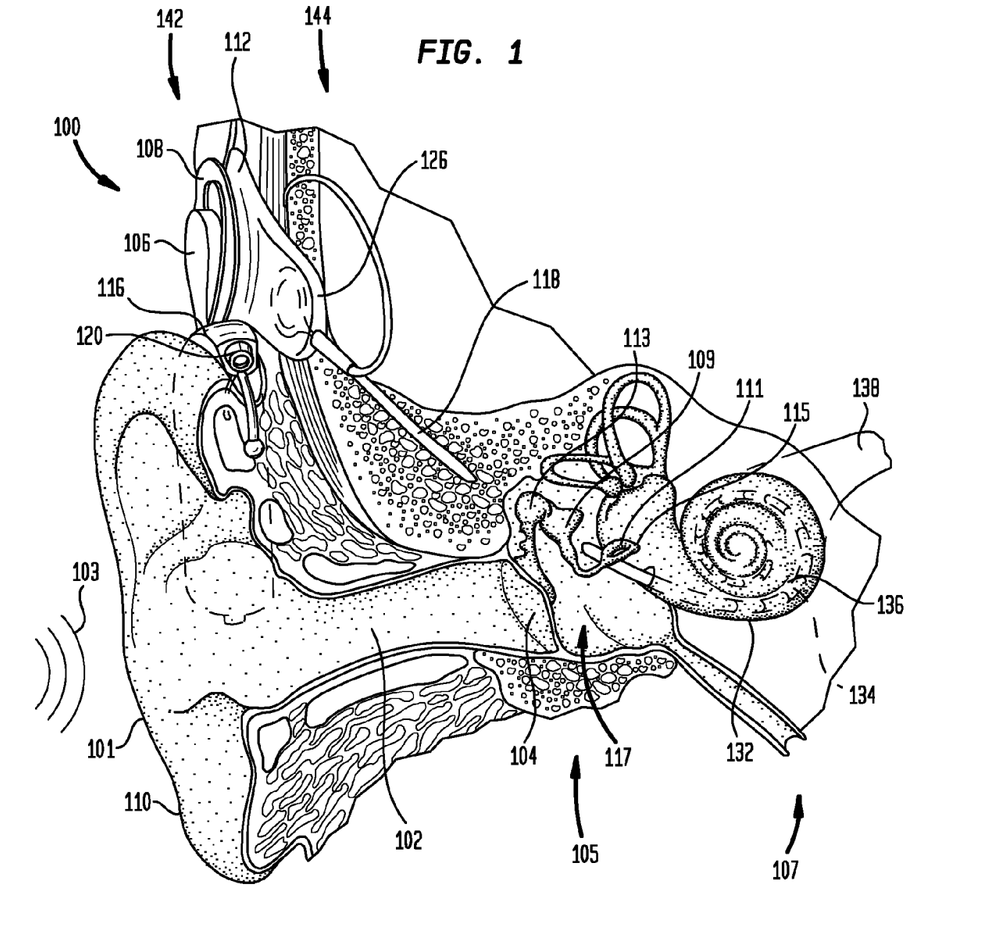
FIG. 1 is a schematic block diagram of one embodiment of an exemplary prosthetic hearing implant suitable for implementing embodiments of the present invention.

FIG. 1 is a perspective view of an exemplary cochlear implant system in which embodiments of the present invention may be implemented. The relevant components of outer ear 101, middle ear 105 and inner ear 107 are described next below. An acoustic pressure or sound wave 103 is collected by outer ear 101 (e.g., the auricle) and channeled into and through ear canal 102. Disposed across the distal end of ear canal 102 is a tympanic membrane 104 which vibrates in response to acoustic wave 103. This vibration is coupled to oval window or fenestra ovalis 115 through three bones of middle ear 105, collectively referred to as the ossicles 117 and comprising the malleus 113, the incus 109 and the stapes 111. Bones 113, 109 and 111 of middle ear 105 serve to filter and amplify acoustic wave 103, causing oval window 115 to articulate, or vibrate. Such vibration sets up waves of fluid motion within cochlea 132. Such fluid motion, in turn, activates tiny hair cells (not shown) that line the inside of cochlea 132. Activation of the hair cells causes appropriate nerve impulses to be transferred through the spiral ganglion cells (not shown) and auditory nerve 138 to the brain (not shown), where they are perceived as sound.

Cochlear implant 100 comprises external component assembly 142 which is directly or indirectly attached to the body of the recipient, and an internal component assembly 144 which is temporarily or permanently implanted in the recipient. External assembly 142 typically comprises one or more audio pickup devices (e.g., microphone(s)) 120 for detecting sound, a speech processing unit 116, a power source (not shown), and an external transmitter unit 106. External transmitter unit 106 comprises an external coil 108 and, preferably, a magnet (not shown) secured directly or indirectly to the external coil 108. Speech processing unit 116 processes the output of audio pickup device (e.g., microphone) 120 that is positioned, in the depicted embodiment, by ear 110 of the recipient. Speech processing unit 116 generates coded signals, referred to herein as a stimulation data signals, which are provided to external transmitter unit 106 via a cable (not shown). Speech processing unit 116 is, in this illustration, constructed and arranged so that it can fit behind outer ear 101 (e.g., the auricle). Alternative versions may be worn on the body or it may be possible to provide a fully implantable system which incorporates the speech processor and/or microphone into the internal component assembly 144.

Internal components 144 comprise an internal receiver unit 112, a stimulator unit 126 and an electrode assembly 118. Internal receiver unit 112 comprises an internal transcutaneous transfer coil (not shown), and preferably, a magnet (also not shown) fixed relative to the internal coil. Internal receiver unit 112 and stimulator unit 126 are hermetically sealed within a biocompatible housing. The internal coil receives power and data from external coil 108, as noted above. A cable or lead of electrode assembly 118 extends from stimulator unit 126 to cochlea 132 and terminates in an array 134 of electrodes. Signals generated by stimulator unit 126 are applied by the electrodes of electrode array 134 to cochlear 132, thereby stimulating the auditory nerve 138.

In one embodiment, external coil 108 transmits electrical signals to the internal coil via a radio frequency (RF) link. The internal coil is typically a wire antenna coil comprised of at least one and preferably multiple turns of electrically insulated single-strand or multi-strand platinum or gold wire. The electrical insulation of the internal coil is provided by a flexible silicone molding (not shown). In use, internal receiver unit 112 may be positioned in a recess of the temporal bone adjacent to ear 110 of the recipient.

Further details of the above and other exemplary prosthetic hearing implant systems in which embodiments of the present invention may be implemented include, but are not limited to, those systems described in U.S. Pat. Nos. 4,532,930, 6,537, 200, 6,565,503, 6,575,894 and 6,697,674, which are hereby incorporated by reference herein in their entireties. For example, while cochlear implant 100 is described as having external components, in alternative embodiments, cochlear implant 100 may be a totally implantable prosthesis. In one exemplary implementation, for example, speech processing unit 116, including the microphone, speech processor and/or power supply may be implemented as one or more implantable components. In one particular embodiment, speech processing unit 116 may be contained within the hermetically sealed housing used for speech processing unit 116.

In one example, electrode array 134 may include a plurality of independent electrodes each of which may be independently stimulated. For example, in an embodiment, employing Cochlear's Nucleus 24 system, electrode array 134 includes 22 independent electrodes each of which stimulates a distinct area of the basilar membrane 136 of the recipient's cochlea 132. As one of ordinary skill in the art is aware, low-frequency sounds stimulate the basilar membrane most significantly at its apex, while higher frequencies more strongly stimulate the basilar membrane's base. Thus, electrodes of electrode array 134 located near the base of the cochlea are used to simulate high frequency sounds while electrodes near the apex are used to simulate low frequency sounds. Typically, in such a system, speech processing unit 116 stimulates only the electrodes with the largest signals. For example, system 100 may estimate the outputs for each of the 22 electrodes and select the ones with the largest amplitude (i.e., maxima). The number of maxima selected may vary, for example, between five (5) and ten (10), depending on a variety of factors. Moreover, the rate of stimulation, often referred to in units of pulses per second (pps), may also vary. Each of the applied maxima will be referred to herein as a channel of stimulation (or stimulation channel). Thus, in an example in which 8 maxima are applied, the system will be described as applying eight (8) channels of stimulation.

As one of ordinary skill in the art will appreciate, the present invention may be used in combination with any speech strategy now or later developed, including but not limited to, Continuous Interleaved Sampling (CIS), Spectral PEAK Extraction (SPEAK), and Advanced Combination Encoders (ACE™). An example of such speech strategies is described in U.S. Pat. No. 5,271,397, the entire contents and disclosures of which is hereby incorporated by reference herein. The present invention may also be used with other speech coding strategies now or later developed. In one embodiment, the present invention may be used on Cochlear Limited's Nucleus™ implant system that uses a range of coding strategies alternatives, including SPEAK, ACE™, and CIS. Among other things, these strategies offer a trade-off between temporal and spectral resolution of the coded audio signal by changing the number of frequency channels chosen in the signal path.

Figure 2A:
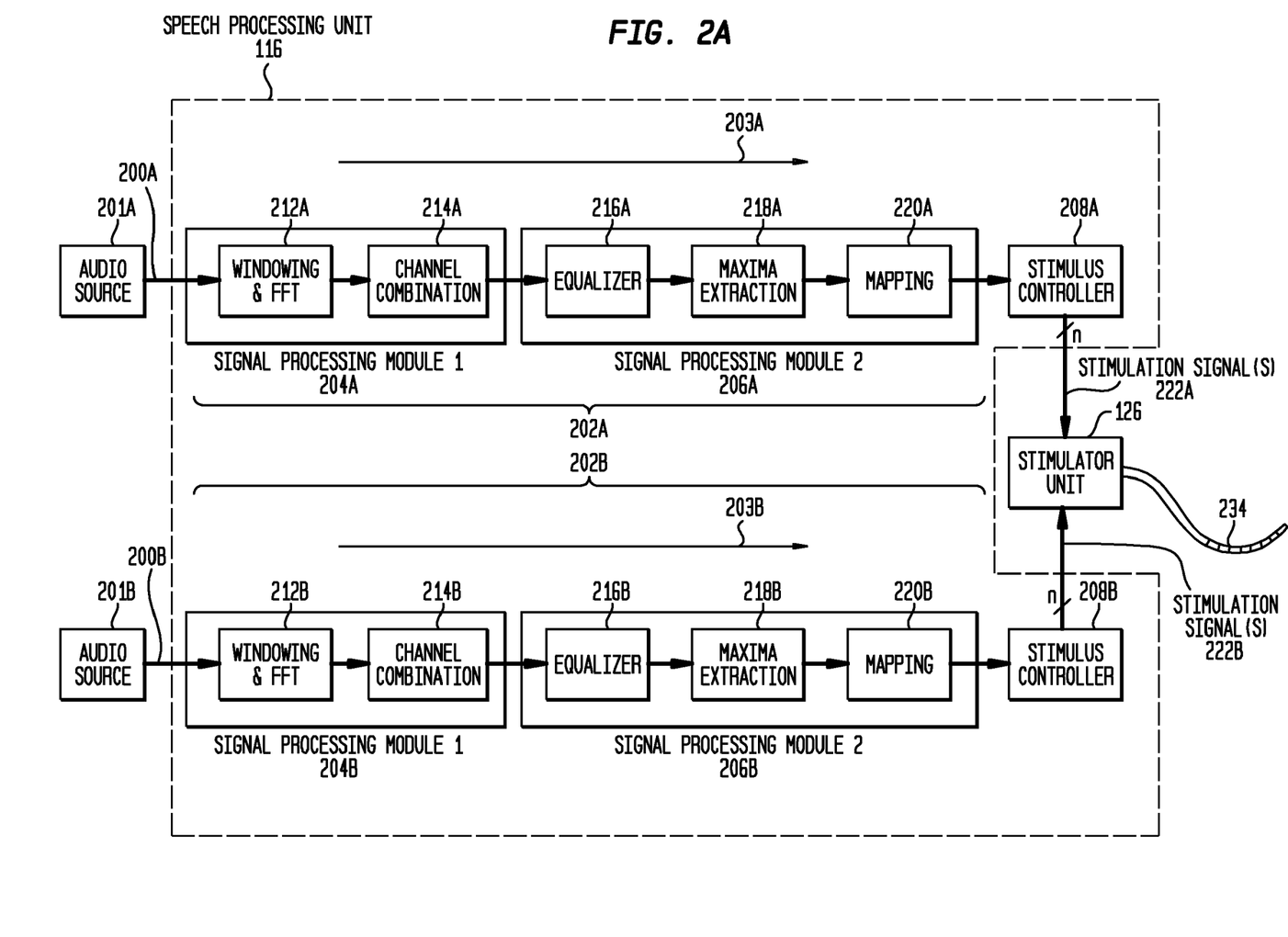
FIG. 2A is a simplified functional block diagram of a speech processor implementing an embodiment of the present invention.
Figure 2B:
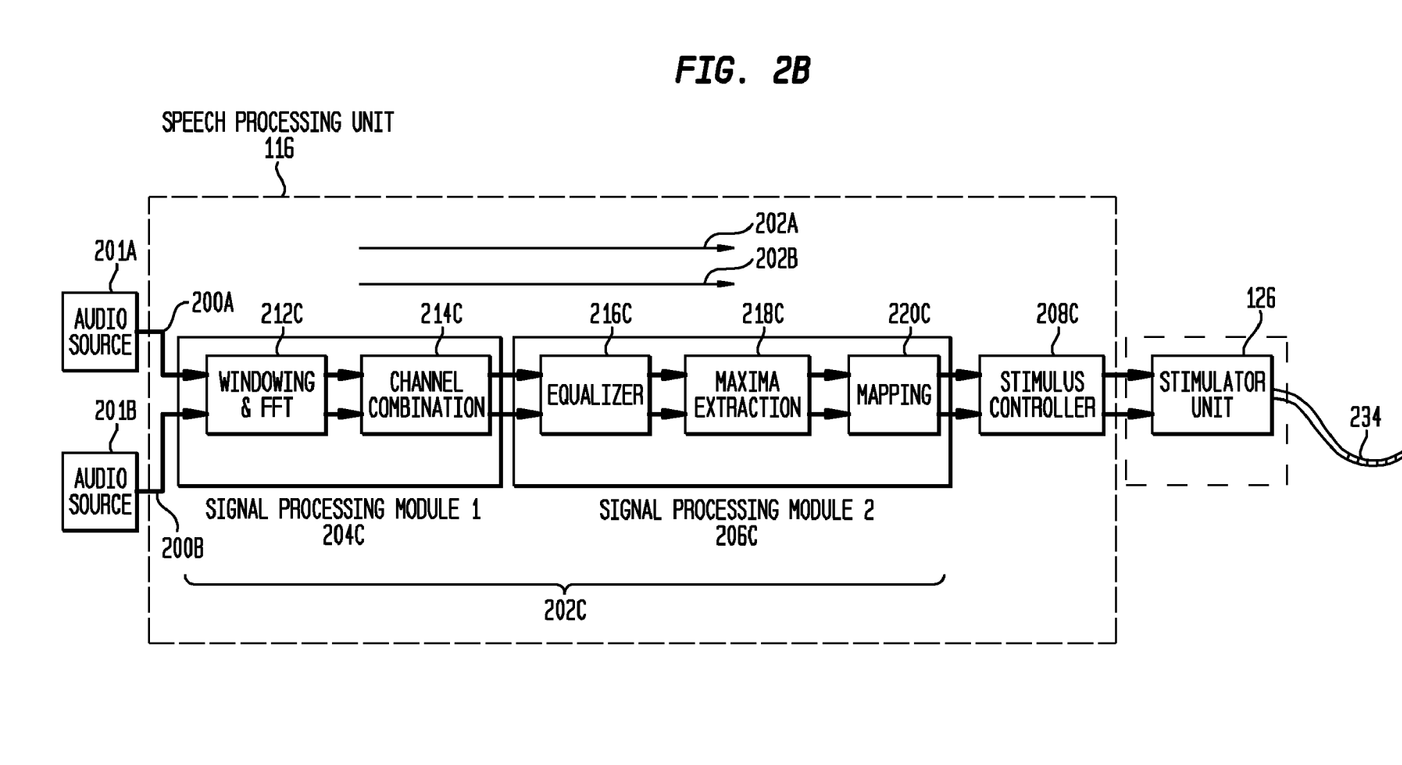
FIG. 2B is a simplified functional block diagram of a speech processor implementing another embodiment of the present invention.

FIGS. 2A and 2B are functional block diagrams of two exemplary embodiments of relevant portions of speech processor 116 configured in accordance with the teachings of the present invention. As noted above, in the presently described embodiments, speech processing unit 116 independently and concurrently processes multiple audio input signals. In doing so, speech processing unit 116 may use separate hardware and software for processing each audio input signal, the same hardware and software for processing each signal, or any combination thereof. In embodiments employing a combination of common and separate hardware and software, the point along the audio processing path in speech processing unit 116 at which the hardware and/or software components are duplicated can vary depending on the implemented embodiment. For example, in the embodiment shown in FIG. 2A there are two audio processing paths 203A and 203B each formed with a dedicated hardware pipeline 202A, 202B, respectively, to process a corresponding audio input signal 200A, 200B, respectively, received from a corresponding audio source 201A, 201B, respectively. In the embodiment shown in FIG. 2B, there are two audio processing paths 203A and 203B through the same hardware pipeline 202C to process corresponding audio input signals 200A, 200B, respectively, received from a corresponding audio sources 201A, 201B, respectively. In other words, in the embodiment shown in FIG. 2A, separate hardware (and software if implemented) is used for processing both audio signals 200A and 200B. In such an embodiment, the functionally-segregated hardware may be attained by, for example, implementing one or more dedicated ASICs in each hardware pipeline 202A, 202B. In contrast, in FIG. 2B the same hardware performs separate operations to process audio signal 200A and audio signal 200B. In this embodiment, the separate operations may be performed by separate software applications, or may be successively or otherwise separately performed by the same software applications. It should be appreciated that these exemplary embodiments utilize pipelining, a signal processing strategy that is well known to those of skill in the art, and as such, is not described further herein.

FIGS. 2A and 2B, for exemplary purposes, illustrate two audio sources 201A and 201B for generating audio signals 200A and 200B, respectively. In various embodiments, audio sources 201 may include, but are not limited to, different microphones or other audio pickup devices, the same or different audio playback devices, the same or different memory devices integrated within or operably coupled to the implementing cochlear implant, etc. As one of ordinary skill in the art would appreciate, any quantity of audio signals from any quantity of audio sources (e.g., one or more) may be processed in accordance with the teachings of the present invention.

After receiving audio signals 200A and 200B, speech processing unit 116, in the presently described embodiments, separately and concurrently processes audio signals 200A and 200B to generate corresponding sets of one or more stimulation signals 222A and 222B, respectively. These stimulations signals may each be distributed across one or more stimulation channel(s). After generation, stimulation signals 222 may be separately provided to electrodes 234, where they may be applied to the same, some of the same, or different electrodes 234. In addition, stimulation signals 222 may be provided to electrodes 234 at successive time intervals. For example, should two stimulation signals generated from different audio signals 200A and 200B be mapped to a same stimulation channel, one stimulation signal may be provided to a first electrode 234 located in the appropriate location in the cochlea, while the other stimulation signal may be provided to the same or a neighboring electrode 234, which is also located in the appropriate location in the cochlea. In other words, the stimulation signals may be delivered to the same or alternating electrodes from time to time, depending on the frequency content of the represented audio signal.

After receiving audio signals 200A and 200B, speech processing unit 116 independently and concurrently processes each signal along signal processing path 203A, 203B to generate respective stimulation signals 222A and 222B. Speech processing unit 116 then provides the generated stimulation signals 222A and 222B to stimulator unit 126, which activates the appropriate electrode(s) 234 of electrode array 134, as noted above.

As shown, signal processing pipeline 202 comprises a first signal processing module 204 and a second signal processing module 206. Each respective processing module, as shown, includes a plurality of functional blocks, which will now be further described. After receipt, audio signal 200 is provided to first signal processing module 204, where it is multiplied by a smoothing window and filterbank process 212. This process 212 preferably uses a Fast Fourier Transform (FFT) to produce a plurality of signals (e.g., 64). These signals are then processed by channel combination unit 214 which may, if necessary, combines the signals to match the number of electrodes 234. For example, in conventional systems, the number of electrodes 234 of the electrode array may be different than the number of signals generated by window and filterbank module 212. As an example, window and filterbank module 212 may output 64 signals, each corresponding to a frequency band of a received audio signal 200. If electrode array 134 only includes, for example, 22 electrodes 234, channel combination unit 214 may combine the received 64 signals to produce 22 separate signals, each corresponding to one electrode. The frequency bands for each of these resulting signals are referred to as channels.

Once channel combination unit 214 combines the signals to match the number of electrodes, the processed signals are sent to second signal processing module 206, where they are provided to an equalizer 216 and a maxima extractor unit 218. Equalizer 216 preferably equalizes the signals; and, maxima extractor unit 218 preferably extracts the resulting largest amplitude signals. The selected largest amplitude signals are referred to as maxima. Once the maxima (e.g., the largest amplitude signals) are chosen, a mapping unit 220 arranges the signals for stimulating corresponding electrodes 234. The signals for the mapped maxima are then provided to a stimulus controller 208. After which, the generated stimulation signals 222A and 222B are provided to stimulator unit 126, where they are used to apply stimuli via electrodes 234 according to the employed speech strategy (e.g., ACE™). The channels corresponding to these stimulation signals are referred to as the applied channels of stimulation (or stimulation channels). Further, a system using, for example, 8 maxima (e.g., the 8 largest amplitude signals) in applying stimuli will be referred to as a system applying 8 channels of stimulation (or stimulation channels).

In an embodiment employing ACE™ on the commercially available SPrint™ speech processor from Cochlear™ Limited, the filterbank process of functional block 212 typically employs a number of analysis filter channels. This number may be varied between 6 and 22, depending on the number of electrodes available and the overall requirements for the filterbank process of functional block 212. If the frequency range of the stimulation channels used by the cochlear prosthesis 100 will be constant, e.g. 80 Hz-8000 Hz, then a setting of 6 (i.e., the number of analysis filters to be employed) will consist of a set of 6 wide filters while a setting of 22 will consist of a set of 22 considerably narrower filters. In some cases, overlapping analysis filters may also be desirable. For example, more filters does not necessarily mean they will be narrower, but rather they may be "more overlapped" with other filters. It is also known that prosthetic hearing implant recipients may be able to make use of both spectral and temporal cues with the stimuli presented to their cochlea, and thus the use of wider filters may provide more temporal information.

Certain embodiments of the present invention may use a filterbank to increase the number of channels to enhance any region of the spectrum where finer spectral detail might be required via many narrow filters. Currently, approximately logarithmic, center frequency spaced filters are typically used in prosthetic hearing implants. An embodiment of the present invention may include a region of high spectral resolution filters within an otherwise logarithmically spaced filterbank. An advantage of certain embodiments of the present invention may be to provide more channels in the filterbank path, so that more channels would become available for selection in the following stages of processing, such as maxima extraction. Channel combination unit 214 may be able to increase the number of available channels for selection by post processing modules 206.

Further, in certain embodiments, the number of channels used may be more than the number of electrodes present in the system. For example, additional "virtual" channels may be placed between existing electrode channels to emphasis certain regions. As an illustration, in one example, an electrode array with 10 electrodes may use 19 channels in processing the audio signal, where 1 "virtual" channel is placed between each real electrode channel. An increased number of channels may allow embodiments of the present invention to more easily accommodate prosthetic hearing implants that have increased numbers of electrodes without major modifications to the implants. Alternatively, embodiments of the present invention may use any number of filters and are not limited to the number of electrodes in the system, since any number of intermediate stimulation sites may be created via mechanisms such as described in U.S. Pat. No. 5,649,970, entitled "Edge-effect electrodes for inducing spatially controlled distributions of electrical potentials in volume conductive media," the entire contents and disclosures of which are hereby incorporated by reference. Any type of filterbank construction now or later developed may be used, such as FIR, IIR or FFT if implemented in a Digital Signal Processor (DSP). With increasing numbers of channels, it often becomes more efficient to use a FFT in filtering the received audio signals.

In one embodiment, the system attempts to retain the independency of the multiple input audio signals by allocating independent channels of stimulation to each input signal. For example, one input signal may be used for listening to the radio or other background noise, while the second input signal is used for listening to speech (i.e., the speech from a person the recipient is engaging in a conversation with). Then, half of the applied channels of stimulation (e.g., 4 maxima in a system using 8 maxima) may be used for the first input signal (e.g., "radio" listening) and the other half (e.g. 4 maxima) for the second input signal (e.g. engaging in a conversation). Because the two input signals (e.g., sound from the radio plus the utterances from a person next) are allocated different sets of stimulation channels (supposedly different cognitive channels), instead of being intermixed before they reach the periphery, the system may improve the recipient's ability to simultaneously engage in a conversation while listening to music (or other background noise). In an alternative embodiment, the system may achieve spatial separation between sound emanating from in front of the recipient and sound emanating from behind the recipient by allocating different sets of stimulation channels to sounds from each direction. An exemplary method which may be implemented in a hearing implant capable of processing multiple sources of input will now be described. This system can be applied, for example, to a system such as that illustrated in FIGS. 2A and 2B.

As noted, each signal processing path 202A, 202B generates respective sets of stimulation signals 222A, 222B, respectively. Signal processing paths 202A and 202B deliver the generated stimulation signals 222A and 222B to implanted stimulator unit 126, which drives one or more electrodes 234 accordingly. In the embodiment shown in FIG. 2B, signal processing pipeline 202C generates respective sets of one or more stimulation signals which are separately delivered to stimulator unit 126, which drives one or more electrodes 234 accordingly.

Figure 3:
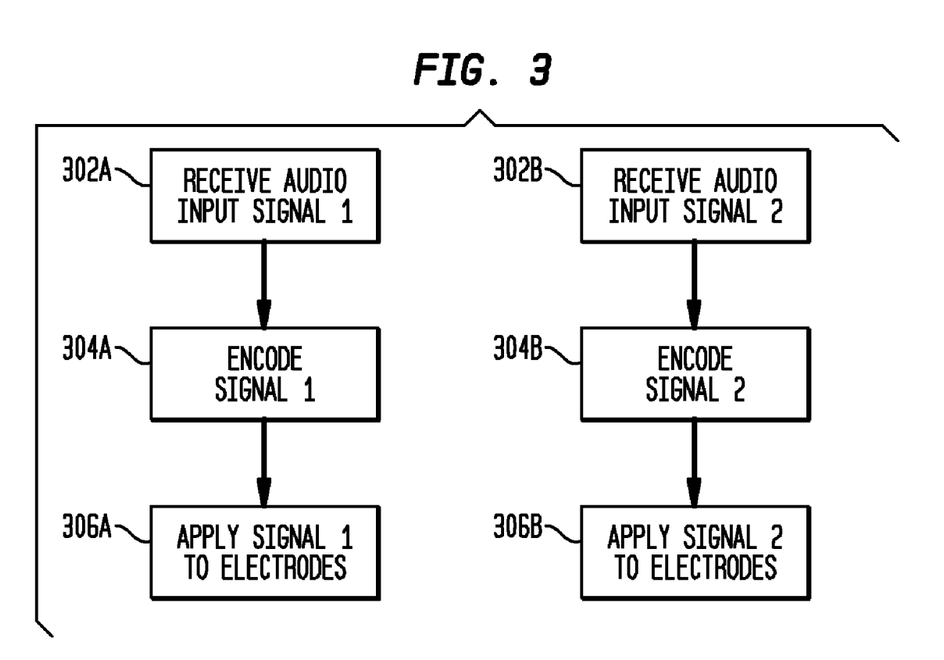
FIG. 3 is a flow diagram of a method for receiving and applying signals from two input sources in accordance with embodiments of the present invention.

FIG. 3 provides a flow chart of an exemplary method of processing multiple audio input signals in accordance with the invention. As shown, audio signals 200A and 200B are separately received at blocks 302A and 302B, respectively. Each input signal may then be processed at blocks 304A and 304B, respectively, to generate a corresponding set of one or more stimulation signals. As noted, any acceptable speech strategy now or later developed may be used for processing audio signals 200A and 200B, such as, for example, Continuous Interleaved Sampling (CIS), Advanced Combination Encoders (ACE™). MULTIPEAK (MPEAK). Spectral Peak (SPEAK), etc. Although in the current embodiment, each audio signal is independently processed, in other embodiments information from one signal may be used in the processing of the other signal. For example, if processing indicates that one signal is a random noise signal (e.g., a loud bang) and the other signal is a speech signal, the processing may use this information to deemphasize the random noise signal by, for example, allocating this signal a lower percentage of the implemented stimulation channels as will be discussed in more detail below. Blocks 302 and 304 may each be performed by speech processing unit 116 using functional blocks such as illustrated in the above discussed FIGS. 2A and 2B.

Each audio signal 200A and 200B is then delivered to each intended set of one or more stimulation channels at blocks 306A and 306B by applying stimuli using the respective generated sets of stimulation signals. That is, stimulator unit 126 may receive the respective sets of stimulations signals and based on these stimulation signals generate signals to cause the electrodes of electrode array 134 to apply corresponding stimuli to cochlea 132.

In a hearing implant system, such as the above-discussed Nucleus 24 implant system, the system may use, for example, 8 maxima at a simulation rate of 1800 pps for a particular user. In such a system, processing block 304 may allocate half of the maxima (i.e., 4 stimulation channels) to one audio signal (e.g., 200A), and the other half (i.e., 4 stimulation channels) to the second audio signal (e.g., 200B). Or in other examples, the applied channels of stimulation may not be equally split but instead weighted in favor of one or more of the plurality of audio signals. Or, in yet another example, each signal may be allocated all 8 maxima, but the signals are alternated in time (i.e., the first signal is applied using all 8 maxima, then the second signal is applied and so on, such that each input signal is applied at a stimulation rate of 900 pps).

It should be appreciated as well that although in the present embodiment each audio signal is allocated the same number of applied stimulation channels (e.g., maxima), in other examples it may be desirable to allocate a larger percentage of the applied channels to one the signals. Or, for example, the system may dynamically determine the number of applied channels of stimulation for each input signal. For example, the system may be designed with a preference towards speech signals. Thus, in such an example, if one of the incoming signals is determined to be carrying speech information, it may be assigned more channels of stimulation (e.g., maxima) than an incoming signal that is determined to be carrying another type of signal.

Or, in yet another example, the system may utilize a multichannel cochlear prosthesis, such as described in U.S. patent application Ser. No. 11/030,980 to Bomjum KWON and Chris Van Den Honert, entitled "A Stimulation Mode for Cochlear Implant Speech Coding," filed on Jan. 10, 2005, which is incorporated by reference herein in its entirety. Such a multi-channel cochlear prosthesis may use multiple modes or techniques of stimulation. These multiple modes of stimulation may include, for example, bipolar stimulation, monopolar (MP) stimulation, variable bipolar stimulation, and common ground (CC) stimulation. In an embodiment using such a multi-channel cochlear prosthesis, one input signal may be provided using one mode (e.g. bipolar), while the other signal is provided using a different mode (e.g., bipolar). Or, in other embodiments, the signals may be applied using a combination of modes, channels of stimulation, and applied frequency.

Further, in another embodiment, the system may analyze each incoming signal and dynamically determine how to apply each input signal. For example, in a system with 5 input signals, the system may dynamically determine to apply one audio signal using a first mode and a subset of channels of the first mode, apply a second audio signal using the same first mode but with a different subset of channels, apply a third audio signal using a second mode but applied at half of its normal frequency, apply a fourth audio signal also using the second mode and at half of its normal frequency but alternating in time with the third signal, and apply the fifth audio signal using a third mode.

Although the above described embodiment provided an example employing two audio sources 201A and 201B (e.g., microphones), in other examples, three or more audio sources (e.g., microphones) may be used. Or, for example, pick up device 120 may include a cord (e.g., a headphone jack) for plugging into the line out of a radio, stereo, or other sound source. Thus, one input audio signal may be received via the cord while another is received via a microphone to allow, for example, the user to listen to music while engaging in a conversation. Or, in yet another example, audio pickup device 120 may be a multi-microphone array with multiple outputs, each distinguishing sounds from different directions. Or, in yet other examples, the different input signals may come from other sources, such as for example, from a signaling source used to notify the user of a particular event, in such an example, it may be desirable to only assign one or two channels of stimulation to such a signal, rather than splitting the applied channels equally.

Although the above described embodiments were discussed with reference to a cochlear implant, in other embodiments these methods and systems may be used with other implant systems such as, for example, in an auditory brainstem implant or an electroacoustical device for a user.

All documents, patents, journal articles and other materials cited in the present application are hereby incorporated by reference. Other embodiments of the invention will be apparent to those skilled in the art from consideration of the specification and practice of the invention disclosed herein. For example, as one of ordinary skill in the art would appreciate, alternative embodiments of a speech processor implementing the present invention may include additional or fewer functional blocks than that illustrated in FIGS. 2A and 2B, or may combine the functions is a manner different than that described above. It is intended that the specification and examples be considered as exemplary only, with a true scope and spirit of the invention being indicated by the following claims.

What is claimed is:

1. A prosthetic hearing implant comprising:
   two or more audio pickup devices each configured to output an audio input signal;
   a speech processing unit configured to independently and concurrently process the two or more audio input signals so as to generate separate sets of stimulation signals, corresponding to said two or more audio input signals, respectively; and
   a stimulator unit configured to apply said sets of stimulation signals to a recipient.

2. The implant of claim 1, wherein said stimulator unit is configured to apply a first one of said sets of stimulation signals to a cochlea of the recipient using a first set of one or more stimulation channels, and to apply a second one of said sets of stimulation signals using a second set of one or more stimulation channels.

3. The implant of claim 2, wherein said second set of one or more stimulation channels comprises at least one stimulation channel which is not included in said first set of stimulation channels.

4. The implant of claim 2, wherein the number of stimulation channels in said first set of one or more stimulation channels is different than the number of stimulations channels in said second set of one or more stimulation channels.

5. The implant of claim 1, wherein said speech processing unit is further configured to select a first mode of stimulation for applying a first one of said sets of stimulation signals, and to select a second mode of stimulation for applying a second one of said sets of stimulation signals.

6. The implant of claim 5, wherein said first and second modes of stimulation are selected from the group comprising: bipolar stimulation, monopolar stimulation, variable bipolar stimulation and common ground stimulation.

7. The implant of claim 1, wherein said stimulator unit is configured to time multiplex said sets of stimulation signals such that said sets of stimulation signals are applied via one or more channels in alternating time slots.

8. The implant of claim 1, wherein said speech processing unit is configured to dynamically set how one or more of said sets of stimulation signals will be applied to the a cochlea of the recipient.

9. The implant of claim 8, wherein said speech processing unit is further configured to dynamically select a mode of stimulation for one or more of said sets of stimulation signals.

10. The implant of claim 1, further comprising:
an electrode array, wherein the stimulator unit is configured to apply a first one of the sets of stimulation signals via the electrode array.

11. The implant of claim 10, wherein the stimulator unit is further configured to apply a second one of the sets of stimulation signals via the electrode array.

12. A prosthetic hearing implant comprising:
two or more audio pickup devices configured to output at least first and second audio signals, respectively;
a speech processing unit configured to receive the at least first and second audio signals and generate a first set of stimulation signals corresponding to the first audio signal, and to concurrently generate at least a second set of stimulation signals corresponding to the second audio signal; and
a stimulator unit configured to apply said at least first and second sets of stimulation signals to a recipient.

13. The implant of claim 12, wherein said stimulator unit is configured to apply said first set of stimulation signals using a first set of one or more stimulation channels, and to apply said second set of stimulation signals using a second set of one or more stimulation channels.

14. The implant of claim 13, wherein said second set of one or more stimulation channels comprise one or more stimulation channels not included in said first set of one or more stimulation channels.

15. The implant of claim 13, wherein the number of stimulation channels in said first set of one or more stimulation channels is different than the number of stimulations channels in said second set of one or more stimulation channels.

16. The implant of claim 13, wherein said stimulator unit is configured to allocate a greater number of stimulation channels to application of said first set of stimulation signals than to application of said second set of stimulation signals, and wherein said allocation is based on the analysis of the first and second audio signals by said speech processing unit.

17. The implant of claim 12, wherein said speech processing unit is further configured to select a first mode of stimulation for applying said first set of stimulation signals, and to select a second mode of stimulation for applying said second set of stimulation signals.

18. The implant of claim 17, wherein said first and second modes of stimulation are selected from the group comprising: bipolar stimulation, monopolar stimulation, variable bipolar stimulation and common ground stimulation.

19. The implant of claim 12, wherein said stimulator unit is configured to time multiplex said first and second sets of stimulation signals such that said sets of stimulation signals are applied via one or more stimulation channels in alternating time slots.

20. The implant of claim 12, wherein said speech processing unit is configured to dynamically set how said first and second sets of stimulation signals will be applied to a cochlea of the recipient.

21. The implant of claim 20, wherein said speech processing unit is further configured to dynamically select a mode of stimulation for said first and second sets of stimulation signals.

22. The implant of claim 12, further comprising:
an electrode array, wherein the stimulator unit is configured to apply the first set of stimulation signals via the electrode array.

23. The implant of claim 22, wherein the stimulator unit is further configured to apply the second set of stimulation signals via the electrode array.

24. A prosthetic hearing implant for stimulating a cochlea of a recipient, comprising:
means for outputting a first audio signal;
means for outputting a second audio signal independent from the first audio signal;
means for concurrently processing said first and second audio signals to generate first and second sets of stimulation signals each corresponding to one of said audio signals; and
means for applying said first and second sets of stimulation signals to the recipient's cochlea.

25. The implant of claim 24, wherein said means for applying said first and second sets of stimulation signals comprises:
means for applying said first set of stimulation signals via a first set of one or more stimulation channels; and
means for applying said second set of stimulation signals via a second set of one or more stimulation channels.

26. The implant of claim 25, wherein said second set of one or more stimulation channels comprise at least one stimulation channel not included in the first set of one or more stimulation channels.

27. The implant of claim 24, wherein said means for applying said first and second set of stimulation signals comprises:
means for applying said first set of stimulation signals using a first mode of stimulation; and
means for applying said second set of stimulation signals using a second mode of stimulation.

28. A prosthetic hearing implant for stimulating a cochlea of a recipient, comprising:
means for simultaneously outputting a plurality of discrete independent audio signals;
means for concurrently generating separate sets of stimulations signals corresponding to each of said audio signals; and
means for concurrently applying said separate sets of stimulation signals to the recipient's cochlea.

29. The implant of claim 28, further comprising:
means for utilizing different modes of stimulation for each of said separate sets of stimulation signals.

30. The implant of claim 28, further comprising:
means for time multiplexing said sets of stimulation signals such that said sets are applied to one or more electrodes in alternating timeslots.

31. A prosthetic hearing implant, comprising:
a first audio pickup device configured to output a first audio input signal;
a second audio pickup device configured to output a second audio input signal independently of and concurrently with the first audio input signal;
a speech processing unit configured to generate a first set of stimulation signals corresponding to said first audio input signal and a second set of stimulation signals corresponding to said second audio input signal; and
a first set of electrodes and a second set of electrodes, wherein the first and second sets of electrodes are free of electrodes common to both of the first and second sets, wherein the implant is configured to apply the first set of stimulation signals to a recipient via the first set of electrodes and the second set of stimulation signals to the recipient via the second set of electrodes.

32. The implant of claim 31, further comprising:
an electrode array, wherein the first set of electrodes is disposed on the electrode array.

33. The implant of claim 32, wherein the second set of electrodes is also disposed on the electrode array.

34. The implant of claim 31, wherein the implant is configured to apply the first and second sets of stimulation signals to a cochlea of the recipient concurrently.

35. The implant of claim 31, wherein the speech processing unit is configured to generate the first and second sets of stimulation signals independently.

36. The implant of claim 31, wherein the speech processing unit is configured to generate the first and second sets of stimulation signals concurrently.

37. The implant of claim 31, further comprising:
stimulator circuitry configured to apply the first and second sets of stimulation signals.

38. The implant of claim 37, wherein the stimulator circuitry comprises a stimulator unit configured to apply the first set of stimulation signals.

39. The implant of claim 38, wherein the stimulator unit is configured to apply the second set of stimulation signals and further configured to apply the first and second sets of stimulation signals concurrently.

* * * * *